United States Patent [19]
DeSantis, Jr. et al.

[11] Patent Number: 5,182,102
[45] Date of Patent: Jan. 26, 1993

[54] ANTI-GLAUCOMA COMPOSITIONS

[75] Inventors: Louis DeSantis, Jr.; Rajni Jani, both of Fort Worth, Tex.

[73] Assignee: Alcon Laboratories, Inc., Fort Worth, Tex.

[21] Appl. No.: 728,920

[22] Filed: Jul. 12, 1991

[51] Int. Cl.$^5$ ............ A61K 9/10; A61K 47/32; A61K 31/135; A61K 31/14
[52] U.S. Cl. .................... 424/78.1; 424/427; 424/428; 424/486; 424/487; 424/501; 424/78.18; 514/772.6; 514/913
[58] Field of Search ............ 424/79, 427, 428, 78.1

[56] References Cited
U.S. PATENT DOCUMENTS

| | | | |
|---|---|---|---|
| 4,256,108 | 3/1981 | Theeuwes | 128/260 |
| 4,911,920 | 3/1990 | Jani et al. | 424/78 |

OTHER PUBLICATIONS

Remingtons Pharmaceutical Sciences, Mack Publishing Co., 1990.
Annual Reports in Medicinal Chemistry, 14:81-87 (1979).
J. Med. Chem., 26:1570-1576 (1983).
J. Med. Chem., 27:503-509 (1984).
J. Med. Chem., 26:7-11, 1561-1569, 1109-1112, 950-957, 649-657, 352-357 (1983).

Primary Examiner—Paul R. Michl
Assistant Examiner—E. J. Webman
Attorney, Agent, or Firm—Julie J. L. Cheng

[57] ABSTRACT

Ophthalmic pharmaceutical compositions useful in controlling elevated intraocular pressure associated with glaucoma and ocular hypertension are described. The compositions comprise a combination of a beta-blocker to reduce the production of aqueous humor and carbachol to enhance the outflow of aqueous humor. A method of controlling elevated intraocular pressure with those compositions is also described.

6 Claims, No Drawings

ANTI-GLAUCOMA COMPOSITIONS

BACKGROUND OF THE INVENTION

The present invention relates to the field of ophthalmology. In particular, the invention relates to the treatment of glaucoma and associated elevations of intraocular pressure and to the treatment of ocular hypertension associated with other diseases or conditions.

Although the underlying causes of glaucoma are not understood, its symptoms often include elevated intraocular pressure, which may be caused either by overproduction of aqueous humor or by inadequate outflow of aqueous humor. If left untreated, or if inadequately treated, glaucoma can lead to blindness or significant loss of vision. There is therefore a continuing need for therapies which control the elevated intraocular pressure associated with glaucoma.

There are currently a number of drugs utilized in the treatment of glaucoma, including: miotics (e.g., pilocarpine, carbachol and acetylcholinesterase inhibitors); sympathomimetics (e.g., epinephrine, dipivalylepinephrine and para-amino clonidine); beta-blockers (e.g., betaxolol, levobunolol and timolol); and carbonic anhydrase inhibitors (e.g., acetazolamide, methazolamide and ethoxzolamide). Miotics and sympathomimetics are believed to lower IOP by increasing the outflow of aqueous humor, while beta-blockers and carbonic anhydrase inhibitors are believed to lower IOP by decreasing the formation of aqueous humor. All four types of drugs have potentially serious side effects. Miotics such as pilocarpine can cause blurring of vision and other, visual side effects, which may lead either to decreased patient compliance or to termination of therapy. Carbonic anhydrase inhibitors can also cause serious side effects which affect patient compliance and/or necessitate the withdrawal of treatment. Moreover, at least one beta-blocker, timolol, has increasingly become associated with serious pulmonary side effects attributable to its effect on beta-2 receptors in pulmonary tissue.

A significant number of glaucoma patients require the administration of more than one type of drug in order to achieve therapeutic control over their intraocular pressure (IOP). That is, a single drug does not provide adequate control of IOP in these patients. Treatment which includes the use of two or more of the above-cited classes of drugs requires the patient to apply the compositions to the affected eye(s) in separate, spaced dosages several times a day. Patient compliance with such complicated dosage regimens can be very poor, particularly with elderly patients. Since the majority of glaucoma patients are elderly, this is a significant problem.

In light of the foregoing circumstances, it is clear that a need exists for new, more potent anti-glaucoma compositions which avoid or reduce the above-cited side effects, while increasing patient compliance. The present invention is directed to such compositions.

SUMMARY OF THE INVENTION

As mentioned above, two or more different types of drugs are sometimes required to achieve therapeutic control of intraocular pressure. The use of a drug which increases outflow of aqueous humor with a drug which reduces aqueous humor formation has the advantage of reducing intraocular pressure via two different mechanisms. Although the basic idea is not new, the discussions concerning this topic have been largely impractical and theoretical in nature.

It has now been found that combinations of at least one beta-blocker and carbachol, when formulated in a composition also including anionic mucomimetic polymers and finely-divided cation exchange resins, provides a solution to the problem of combining a drug to increase outflow of aqueous humor with a drug to reduce aqueous humor formation, and additionally provides comfortable, sustained-released compositions. Thus, the present invention is directed to such anti-glaucoma compositions, as well as methods of controlling IOP utilizing these compositions.

DETAILED DESCRIPTION OF THE INVENTION

The anti-glaucoma compositions of the present invention comprise a combination of carbachol, one or more beta-blockers, anionic mucomimetic polymers and cation exchange resins.

The beta-blockers which are useful in the compositions of the present invention include all presently known beta-blockers which demonstrate the requisite cation charge and intraocular pressure effect. Such betablockers are typically represented by the following generic structure:

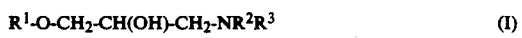

$$R^1\text{-O-CH}_2\text{-CH(OH)-CH}_2\text{-NR}^2R^3 \qquad (I)$$

wherein:

$R^1$ is a substituted or unsubstituted cyclic or aliphatic moiety; cyclic moieties include mono- and polycyclic structures which may contain one or more heteroatoms selected from C, N, and O; and $R^2$ and $R^3$ are independently selected from H and substituted and unsubstituted alkyl.

With regard to Structure (I), above, the following references are hereby incorporated by reference herein: *Annual Reports in Medicinal Chemistry*, 14:81-87 (1979); *J. Med. Chem.*, 26:1570-1576 (1983); ibid., 27:503-509 (1984); ibid., 26:950-957 (1983); ibid., 26:1561-1569 (1983); ibid., 26:1109-1112 (1983); ibid., 26:950-957 (1983); ibid., 26:649-657; and ibid., 26:325-257 (1983). Representative beta-blockers include the racemic and enantiomeric forms of: betaxolol, timolol, metoprolol, befunolol, falintolol, levobunolol, carteolol, mepindolol, pindolol, bisoprolol, bopindolol, atenolol, arotinolol, acebutolol, nadolol, celiprolol, metipranolol, bevantolol, ICI 118,551, pamatolol, penbutolol, toliprolol, tiprenolol, practololm, procinolol, exaprolol, cicloprolol, carazolol, tazolol, tienoxolol, oxprenolol, propranolol, IPS 329, labetolol, dilevalol, esmolol, bupranolol, bunolol, isoxaprolol, diacetolol and the like. The preferred beta-blocker is betaxolol, especially S-betaxolol.

In general, an amount of a beta-blocker less than or equal to about 2.0% by weight (wt%) and amount of carbachol less than or equal to about 5.0 wt% are used. It is preferred that an amount of beta-blocker between about 0.1 and about 1.0 wt% is used and it is especially preferred to use an amount between about 0.25 to about 0.5 wt%. An amount of carbachol between about 0.25 and about 3.0 wt% is preferred and an amount between about 0.75 and about 3.0 wt% is especially preferred. The ratio by weight of beta-blocker to carbachol is generally between about 1:1 to about 1:40, preferably between about 1:6 to about 1:12. The high molecular weight, anionic mucomimetic polymers useful in the present invention have a molecular weight between about 50,000 and 6 million daltons. The polymers are characterized as having carboxylic acid functional groups and preferably contain between 2 and 7 carbon atoms per functional group. The gels which form during preparation of the ophthalmic polymer dispersion have a viscosity between about 1,000 to about 300,000 centipoise (cps). Suitable polymers are carboxy vinyl polymers, preferably those called Carbomers, e.g., Carbopol ® (B.F. Goodrich Co., Cleveland, Ohio). Specifically preferred are Carbopol ® 934 and 940. Such polymers will typically be employed in an amount between about 0.05 and about 8.0 wt%, depending on the desired viscosity of the composition. Pourable liquid compositions generally comprise an amount of the polymer between about 0.05 and about 2.0 wt%.

The cation exchange resins useful in the present invention are characterized as either strongly acidic, such as those having sulfonic acid functionality, or weakly acidic, such as those having carboxylic acid functionality. Such resins are readily available, for example, from Rohm & Haas (Philadelphia, Pa.) under the name Amberlite ® and from Dow Chemical Co. (Midland, Mich.) under the name Dowex ®. The average particle size of the commercially available forms of the resins is about 40 to 150 microns. As the particle size of the resin is critical, such commercially available particles are most conveniently reduced to a particle size range of about 1.0 to 25 microns by ball milling, according to known techniques. At least 95% of the resulting spheroidal particles must have a diameter less than 20 microns. The ion exchange resins will typically be present in an amount between about 0.05 to about 10.0 wt% and will have an average particle size diameter between about 1 to about 20 microns.

These anionic mucomimetic polymers and cation exchange resins are discussed in greater detail in U.S. Pat. No. 4,911,920 issued Mar. 27, 1990. The entire contents of that patent are hereby incorporated by reference herein.

In addition to the above-described principal ingredients, the antiglaucoma compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Onamer M ® and other agents equally well-known to those skilled in the art. Such preservatives, if utilized, will typically be employed in an amount between about 0.001 to 1.0 wt%. Examples of suitable agents which may be utilized to adjust the tonicity or osmolality of the formulations include: sodium chloride, potassium chloride, mannitol, dextrose, glycerin and propylene glycol. Such agents, if utilized, will typically be employed in an amount between about 0.1 to 10.0 wt%.

As will be appreciated by those skilled in the art, the compositions may be formulated in various dosage forms suitable for topical ophthalmic delivery, including solutions, suspensions, emulsions, gels and erodible solid ocular inserts. The compositions are preferably aqueous, have a pH between 3.5 to 8.0 and an osmolality between 280 to 320 milliOsmoles per liter (mOsm/l).

The following examples further illustrate the antiglaucoma compositions of the present invention.

The following formulations are typical ophthalmic suspensions of the present invention.

| INGREDIENT | AMOUNT (wt %) | |
|---|---|---|
| | Formulation A | Formulation B |
| Betaxolol HCl | 0.28* + 5% xs | 0.28* + 5% xs |
| Carbachol | 1.5 | 3.0 |
| Amberlite ® IRP-69+ | 0.25 | 0.25 |
| Carbopol ® 934P | 0.20 | 0.20 |
| Edetate disodium | 0.01 | 0.01 |
| Mannitol | 2.0 | — |
| Benzalkonium chloride | 0.01 + 10% xs | 0.01 + 10% xs |
| NaOH and/or HCl | (to pH 7.4) | (to pH 6.7) |
| Purified Water | q.s. to 100 | q.s. to 100 |

*Equivalent to 0.25 wt % of betaxolol (free base)
+Chemical name: poly(styrenedivinylbenzene) sulfonic acid Each of Formulations A and B were compounded in the following manner. To a suitable formulation vessel containing a stir bar was added approximately 50% of the batch weight of purified water. Stirring was begun and the betaxolol HCl, carbachol and Amberlite ® were added. Stirring was continued for twelve hours, at which point the remaining ingredients were added and the stirring continued until the ingredients were dispersed. The batch weight was then adjusted to approximately 80% by addition of purified water, the pH was adjusted using sodium hydroxide and/or hydrochloric acid, and the weight adjusted to 100% with purified water. The resultant suspension was then sterilized by autoclaving and filled into 5 milliliter (ml) bottles using aseptic techniques.

The present invention is also directed to methods of treating and controlling ocular hypertension associated with glaucoma and other ophthalmic diseases and abnormalities. The methods comprise topically applying to the affected eye(s) of the patient a therapeutically effective amount of a composition according to the present invention. The frequency and amount of dosage will be determined by the clinician based on various clinical factors. The methods will typically comprise topical application of one or two drops (or an equivalent amount of a solid or semi-solid dosage form) to the affected eye one to two times per day.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topical ophthalmic composition for the treatment of glaucoma and ocular hypertensions, comprising: about 0.25 wt% betaxolol; between about 1.5 and about 3.0 wt% carbachol; between about 0.05 and about 8.0 wt% of an anionic mucomimetic polymer; and about 0.05 and about 10.0 wt% of a finely divided cation exchange resin.

2. The composition of claim 1, wherein the concentration of carbachol is about 1.5 wt%.

3. The composition of claim 1, wherein the concentration of carbachol is about 3.0 wt%.

4. A method for treatment of glaucoma and ocular hypertension, comprising applying to an affected eye a composition comprising: about 0.25 wt% betaxolol; between about 1.5 and about 3.0 wt% carbachol; between about 0.05 and about 8.0 wt% of an anionic mucomimetic polymer; and between about 0.05 and about 10.0 wt% of a finely divided cation exchange resin.

5. The method of claim 4, wherein the concentration of carbachol is about 1.5 wt%.

6. The method of claim 4, wherein the concentration of carbachol is about 3.0 wt%.

* * * * *